United States Patent [19]
Wood et al.

[11] Patent Number: 5,863,360
[45] Date of Patent: Jan. 26, 1999

[54] SURFACE TREATMENT OF SHAPE MEMORY ALLOYS

[75] Inventors: John Vivian Wood, Bedford; David Malcolm Grant; Sarah Margaret Green, both of Nottingham, all of United Kingdom

[73] Assignees: The University of Dundee, Dundee; The University Nottingham, Nottingham, both of United Kingdom

[21] Appl. No.: 704,635

[22] PCT Filed: Mar. 6, 1995

[86] PCT No.: PCT/GB95/00486

§ 371 Date: Nov. 19, 1996

§ 102(e) Date: Nov. 19, 1996

[87] PCT Pub. No.: WO95/23876

PCT Pub. Date: Sep. 8, 1995

[30] Foreign Application Priority Data

Mar. 5, 1994 [GB] United Kingdom .................. 9404268

[51] Int. Cl.[6] ............................. C22C 19/03; C22K 1/00
[52] U.S. Cl. ......................... 148/561; 148/563; 148/402; 148/403; 433/20; 606/228
[58] Field of Search .................................... 148/561, 563, 148/462, 403; 433/20; 606/228

[56] References Cited

U.S. PATENT DOCUMENTS 4,411,711  10/1983  Albrecht et al. ........................ 148/563
5,137,446  8/1992  Yamauchi et al. ........................ 433/20
5,232,361  8/1993  Sachdeva et al. ........................... 433/8

FOREIGN PATENT DOCUMENTS 7-126780   5/1995  Japan .
8-109455   4/1996  Japan .
WO 91/12771  9/1991  WIPO .

OTHER PUBLICATIONS

Oshida, Y. et al, "Effects of Shot–Peening on Surface Contact Angles of Biomaterials," Journal of Materials Science: Materials in Medicine, vol. 4, No. 5, 1993, pp. 443–447.

Koike, H. et al, "Crystal–to Amorphous Transformation of NiTi Induced by Cold Rolling," Journal of Materials Research, vol. 5, No. 7, Jul. 1990, pp. 1414–1418.

*Primary Examiner*—George Wyszomierski
*Attorney, Agent, or Firm*—Smith-Hill and Bedell

[57] ABSTRACT

A method of treatment of a shape memory alloy involves shot peening of the alloy sample, thereby causing a crystal to amorphous transition of a surface layer of the sample without substantially affecting bulk characteristics of the material, particularly its shape memory behavior and biocompatibility. The method may be used for surface hardening and to reduce coefficients of friction. The method may be advantageously used for treating tissue sutures and orthodontic devices such as dental archwires.

13 Claims, 4 Drawing Sheets

SURFACE TREATMENT OF SHAPE MEMORY ALLOYS

The present invention concerns a method of surface treatment of a shape memory alloy, and in particular the surface hardening of a nickel-titanium NiTi shape memory alloy by shot peening.

The term shape memory alloy is used in this Specification to refer to an alloy which recovers from a deformed shape to a pre-formed, substantially stress-free shape on being subjected to certain conditions. Such alloys are known within the art and have a variety of uses. For example, NiTi alloy is used in surgical remote tissue suturing wherein the suture may conveniently be introduced into the body in a deformed shape but subsequently may recover the pre-formed shape by virtue of the superelastic properties of the material, thereby automatically having the required suturing effect.

One particular disadvantage is that shape memory alloys are relatively soft materials, with the result that they may for this reason be unsuitable for certain uses to which they might otherwise be applied. Moreover, any surface hardening of the material attempted to overcome this problem must naturally not cause loss of desirable bulk characteristics of the material such as the shape memory behaviour or, in the cited example, the biocompatibility of the material.

The present invention seeks to mitigate or obviate these or other difficulties.

According to the invention there is provided a method of surface treating a shape memory alloy in which method a sample of the alloy to be treated is shot peened to modify the structure of a surface layer of the alloy, whereby bulk material characteristics of the sample are substantially unaffected.

According to the invention there is further provided a method of surface treating a NiTi shape memory alloy by shot peening a sample of the alloy to cause a crystal to amorphous transition of a surface layer of the alloy, whereby bulk material characteristics of the sample are substantially unaffected.

The method may further comprise preliminary forming and annealing of the sample to establish the shape memory. The annealed sample may be polished prior to peening.

Preferably there is used glass peening media. The pressure of the air jet carrying the media may be from 3 to 7 bar. Preferably the sample is maintained at a constant distance from the jet nozzle. The peening time may be between 30 and 60 seconds.

The method may further comprise the step of ultrasonically cleaning the sample after peening.

According to the invention there is further provided a shape memory alloy which has been surface treated by a method according to any of the preceding five paragraphs.

According to the invention there is further provided a tissue suture which has been treated by a method as hereinbefore described.

According to the invention there is further provided dental apparatus which has been treated by a method as hereinbefore described. The apparatus may be an orthodontic device, and may in particular be a dental archwire.

According to the invention there is further provided a method of remote tissue suturing comprising the steps of providing an elongate suture of a shape memory alloy, constraining the suture in a required suturing configuration and so treating the suture as to create a substantially stress-free structure in the suturing configuration, re-forming the suture into a further configuration, introducing the suture into the required suturing site whilst restrained in the further configuration and subsequently permitting the suture to return to the suturing configuration by virtue of its shape memory characteristics thereby effecting remote tissue suturing.

The alloy is preferably a nominally equiatomic NiTi alloy. The alloy may be selected or modified to have a shape memory retention temperature greater than the maximum temperature to which the suture is expected to be subjected in use, for example during sterilisation.

Preferably the suture is wound around a suitable mandrel to form a helix of a predetermined diameter. The suture may be subjected to a stress-relieving heat treatment to form a substantially stress-free helix possessing superelastic properties. Preferably the suture is surface treated by a method as hereinbefore described.

Preferably the helix is subsequently opened and constrained within a rigid elongate tube. The tube and the enclosed suture may be introduced to the required suturing site. Preferably the suture is then extruded from the tube so that the suture regains the suturing configuration by superelastic recovery.

BRIEF DESCRIPTION OF THE DRAWINGS

The invention will be further described with reference to the following examples, and to the accompanying drawings in which.

DETAILED DESCRIPTION OF THE INVENTION

Example 1

Figure 1:
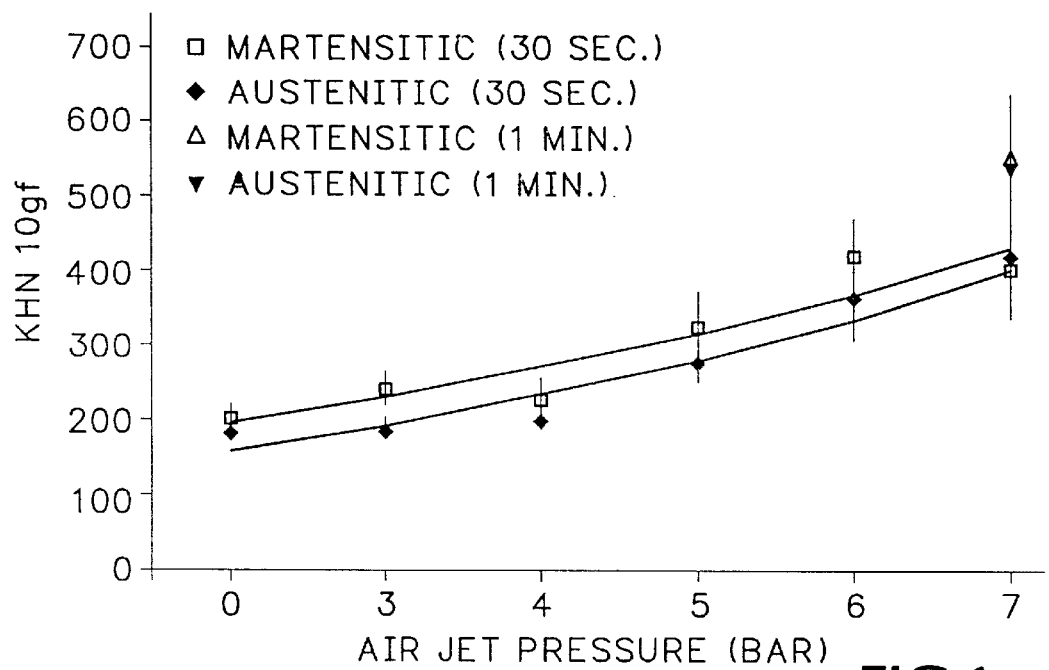
FIG. 1 is a graph of Knoop hardness against peening intensity.

Austenitic and martensitic forms of NiTi alloy were used in this study. Both alloys were manufactured by the Furukawa Electric Co. and had transformation temperatures of 302K for the austenitic and 365K for the martensitic material, which were determined using differential scanning calorimetry (DSC). The compositions of the alloys, determined using energy dispersive X-rays (EDX), were Ni-48.9 at % Ti for the austenitic and Ni-51.8 at % Ti for the martensitic material. The alloys were supplied in as rolled strip form from which 3 mm diameter discs were punched. The discs were annealed at 873K for 30 minutes in a dynamic argon atmosphere. The annealed samples were polished on abrasive SiC paper followed by 6 and 1 $\mu$m diamond pastes. The samples were peened using glass peening media. Peen conditions were varied by adjusting the pressure of the air jet carrying the peening media and the time of peening exposure. The samples were kept at a constant distance from the jet nozzle during the peen. Table 1 gives the back air pressures and durations used. Three samples of each condition were produced. Once peened, the samples were ultrasonically cleaned in ethanol.

TABLE 1

Shot peening back air jet pressures and peening times.

| Air Jet Pressure (Bar) | Martensitic Time(s) | Austenitic Time(s) |
|---|---|---|
| 7 | 60 | 60 |
| 7 | 30 | 30 |
| 6 | 30 | 30 |
| 5 | 30 | 30 |
| 4 | 30 | 30 |
| 3 | 30 | 30 |
| None | N/A | N/A |

Differential scanning calorimetry, using a DuPont 990 Thermal Analyser, was used to monitor the transformation characteristics of one set of peened samples. The DSC sample weight was approximately 18 mg. A second set of samples was used for microhardness and friction measurements. A Knoop microindenter with a 10 gf load was used. The frictional behaviour of the peened surfaces was measured using a 1.8N load acting on a hardened 5 mm diameter tungsten carbide ball. The amplitude of oscillation was 100 $\mu$m and the frequency used was 8 Hz. The third set of samples was jet polished for TEM examination. In order to examine the peened surface the jet polishing was carried out from one side only using a 30:70 $HNO_3:CH_3OA$ mix at 243K and 10 V. The thinned discs were examined in a JEOL 2000FX TEM operating at 200 KeV.

To provide comparative measurements, $N^+$ ion implanted samples implanted at 100 KeV with ion doses ranging from $2 \times 10^{13}$ $cm^{-2}$ to $3 \times 10^{17}$ $cm^{-2}$ were also examined using DSC, TEM, friction and microhardness. $N^+$ ion implantation into equiatomic NiTi is known to produce amorphisation for ion doses in excess of $1 \times 10^{15}$ $cm^{-2}$.

RESULTS

TEM examination of the peened samples showed that regions of the surface structure were partially amorphous for both the austenite and martensite samples peened at 7 and 6 bar air pressures. The corresponding ring selected area diffraction pattern (SADP) confirms the amorphous nature. An EDX spectrum confirmed the amorphous regions to have compositions of nominally equiatomic NiTi. In a bright field micrograph of a thinned martensitic sample peened at 6 bar back air pressure, limited areas of electron transparent material due to surface unevenness were apparent. The amorphous regions were found at the periphery of the peen indents. DSC analyses showed the peened and unpeened samples to have similar transformation behaviour in both the austenite and martensite cases. The level of peen used in this study made no apparent difference to the energy of transformation or the austenite start and finish temperatures. The samples treated by $N^+$ ion implantation were also examined in the DSC and were also found to have similar transformation characteristics.

The Knoop microindentation results are summarised in FIG. 1 and show an increase in Knoop microhardness for both martensitic and austenitic material for peening levels in excess of 4 bar back air jet pressure. The unpeened hardnesses of both materials of around 200 $KHN_{10gf}$ of increased to in excess of 500 $KHN_{10gf}$ after the heaviest peen of 7 bar for 1 minute. The Knoop microhardness of the $N^+$ ion implanted samples increased with ion dose from around 130 $KHN_{10gf}$ for unimplanted material to around 300 $KHN_{10gf}$ for an $N^+$ ion dose of $2 \times 10^{17}$ $cm^{-2}$.

Figure 2:
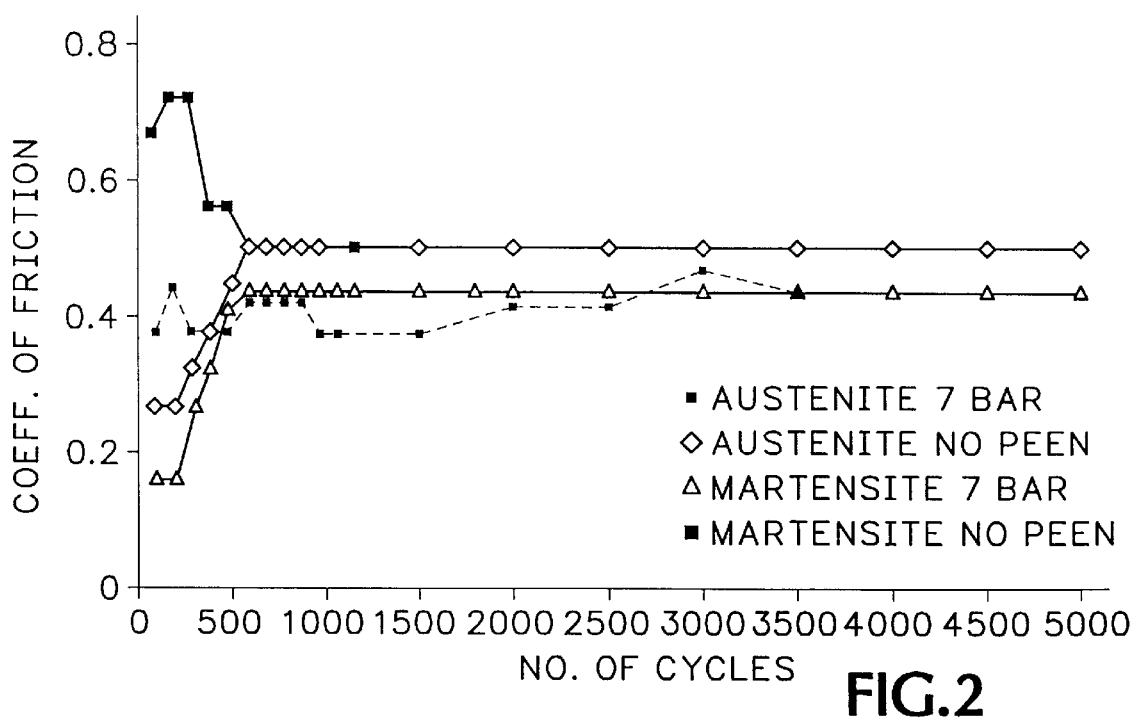
FIG. 2 is a graph showing coefficients of friction of peened materials.

The coefficient of friction results for the peened material are summarised in FIG. 2. The lowest coefficient of friction for both the austenite and martensite peened samples for greater than 1000 cycles was found for material treated at the highest peening intensity of 7 bar back air pressure. The initially higher friction value for the unpeened martensitic sample is thought to be the result of martensite accommodation in the area of ball/sample contact.

The ion implanted material (only a martensitic composition in this case) showed a lowering in coefficient of friction with increasing ion dose. In comparison to the peened samples the ion implanted material showed a more gradual increase in friction with the number of cycles with constant behaviour attained after 2500 cycles.

DISCUSSION AND CONCLUSIONS

The TEM micrographs of the peened samples showed complicated image contrast typical of the samples having undergone extensive deformation. In the regions of highest plastic deformation, such as the peen indents, amorphous areas were observed in the highly peened samples. This amorphous transformation is believed to be the result of the energetic instability of the heavily cold worked crystal. The increased dislocation density produced during heavy peening (witnessed by the TEM studies) has the effect of raising the free energy of the crystal to a level above that of the amorphous phase. Because of this, the transformation to the amorphous phase is energetically permitted. Dislocation densities of $10^{14}$ $cm^{-2}$ have been reported in areas surrounding amorphous bands in cold rolled NiTi. The corresponding elastic strain energy of this dislocation density was calculated to be of the same order as the crystallisation energy of amorphous NiTi.

Consideration of the mechanics of the peening parameters enabled a calculation to be made of the impact stresses involved in the creation of the partially amorphous samples. Measurements were made of the average grit velocity, diameter and density in order to calculate the mean pressure of an incoming grit particle whilst measurement of the peen indent depth enabled calculation of the mean stress per impact for a grit particle hitting the sample normally. The calculated mean stress per impact acting on a 7 bar sample was found to be approximately $1.2 \times 10^5$ $Nms^{-2}$ and $1.0 \times 10^5$ $Nms^{-2}$ for a 6 bar sample. Over the duration of a 1 minute peen at 7 bar, $\approx 18000$ such impacts will occur, whilst approximately one quarter as many will occur over 30 seconds at 6 bar air jet pressure.

The Knoop indentation results show similar trends for both the ion implanted and shot peened material, with a correlation found between increased hardness and increased tendency to amorphisation. Owing to the shallow projected depth of the implanted ion surface layer, the Knoop hardness values measured for the ion implanted material include contributions from both the bulk material and the implantation affected material. The measured depth of a typical Knoop indentation being around 10 $\mu$m whereas the ion affected layer is only around 0.13 $\mu$m deep for $N^+$ ions implanted at 100 KeV.

The lowering of the coefficient of friction with increasing amorphous nature has previously been shown in ion implanted NiTi. Similarly, in the present study the highest peening level produced consistently lower values of coefficient of friction for both austenitic and martensitic samples. However, altered surface topography due to shot peening has been proposed as a mechanism for the reduction in the frictional behaviour of some ferrous samples.

The DSC results showed that the very shallow modified surface layer produced by both peening and ion implantation treatments had no detectable effect upon the bulk material transformation characteristics. This result is significant, allowing considerable surface improvements to be realised for both martensite and austenitic material without detriment to the shape memory/superelastic behaviour.

Example 2

Figure 3:
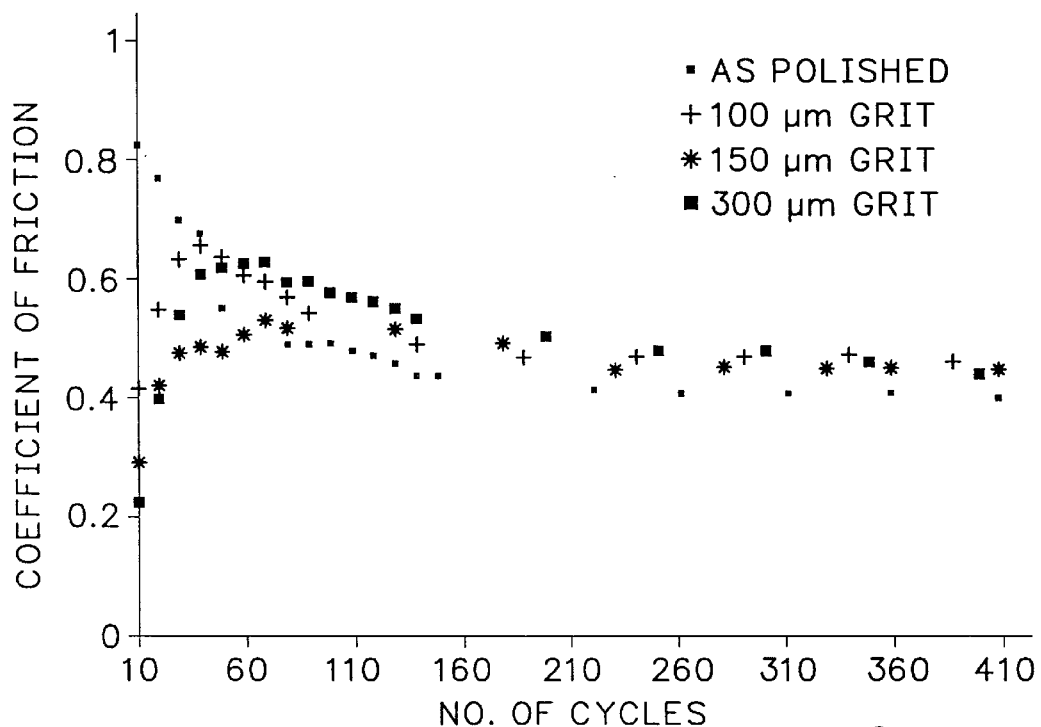
FIG. 3 is a graph showing ball-on-flat friction behaviour of austenitic NiTi shot peened material.
Figure 4:
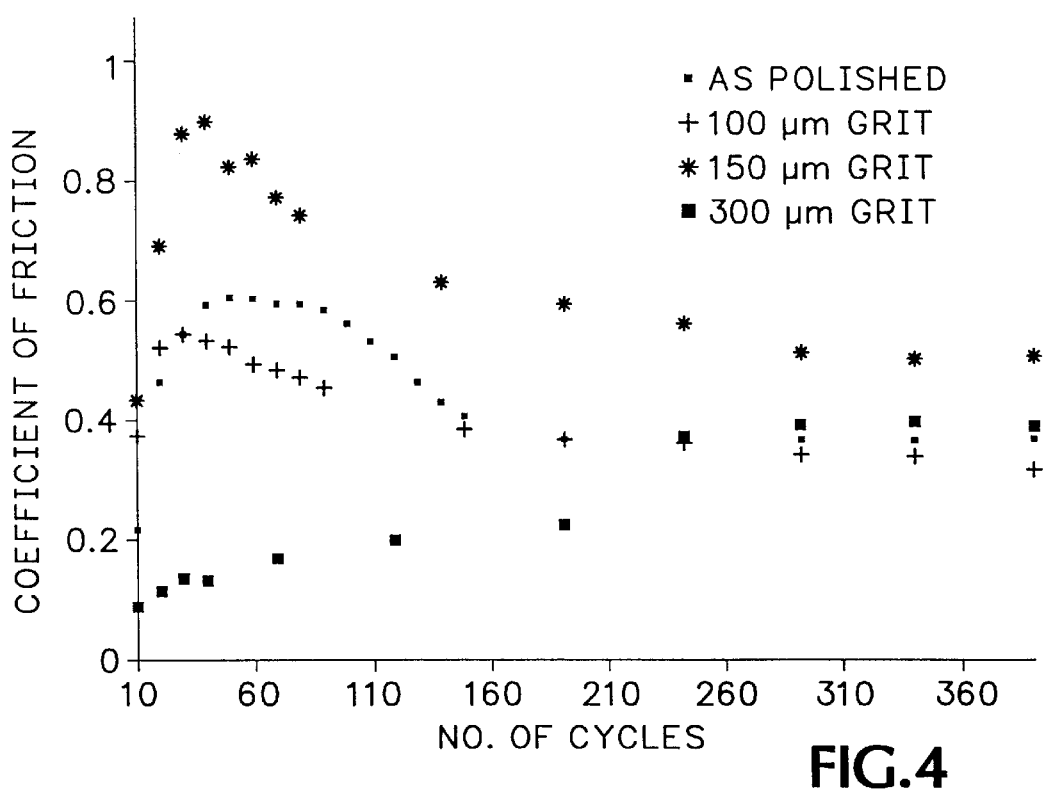
FIG. 4 is a graph showing ball-on-flat friction behaviour of martensitic NiTi shot peened material.

In this Example the relationship between mass of peening particle and the extent of surface modification is explored further. The total energy, in the form of mechanical deformation, that a shot peened Ni-Ti surface is subjected to is a function of the peening media mass. To investigate this relationship, three different sizes of glass peening media were used within the experimental shot peening apparatus, operating at a back air pressure of 7 bar for a duration of 60 seconds. The glass media mean particle size diameters ranged from 100 $\mu$m to 300 $\mu$m. Surface treatments were performed on austenitic and martensitic forms of Ni-Ti shape memory alloy. The frictional behaviour of the treated and untreated polished Ni-Ti samples were assessed using a ball-on-flat friction test rig, the results from which are shown in FIGS. 3 and 4.
(i) Austenitic Material FIG. 3 shows that the coefficient of friction of the Ni-Ti surface, within the first 50 cycles, is favourably lowered by all three of the peening treatments. The initial, <50 cycles, coefficient of friction of the unpeened material is considerably higher than that of the peened material.
(ii) Martensitic Material FIG. 4 shows that the coefficient of friction of the samples peened using 300 $\mu$m grit exhibited a marked reduction in friction for the initial 250 cycles compared to that of the unpeened material.
Conclusion The peening of martensitic material using the largest grit of 300 $\mu$m produced a significant reduction in the coefficient of friction, within the first 250 cycles, compared to that of unpeened material and material peened using the smaller grit sizes. The shot peening of austenitic material using either of the three grit sizes produced a tangible lowering of the coefficient of friction, within the first 50 cycles, as compared to that of unpeened material.

Example 3

SHOT PEEN TREATMENT OF NI-TI DENTAL ARCHWIRES

Ni-Ti superelastic dental archwires are capable of transmitting low and relatively constant tooth moving forces and are consequently used extensively within orthodontics. A uniform distribution of forces across the teeth is desired. The interface between the Ni-Ti archwire and the tooth is facilitated with a stainless steel bracket glued on to each tooth. The lower the coefficient of friction between the bracket and the archwire, the more uniform the tooth moving force will be across the teeth.

The shot peening of austenitic Ni-Ti dental archwires using three different grades of glass peening media was investigated. A marked reduction in the coefficient of friction of archwire/stainless steel interface has been recorded.

Figure 5:
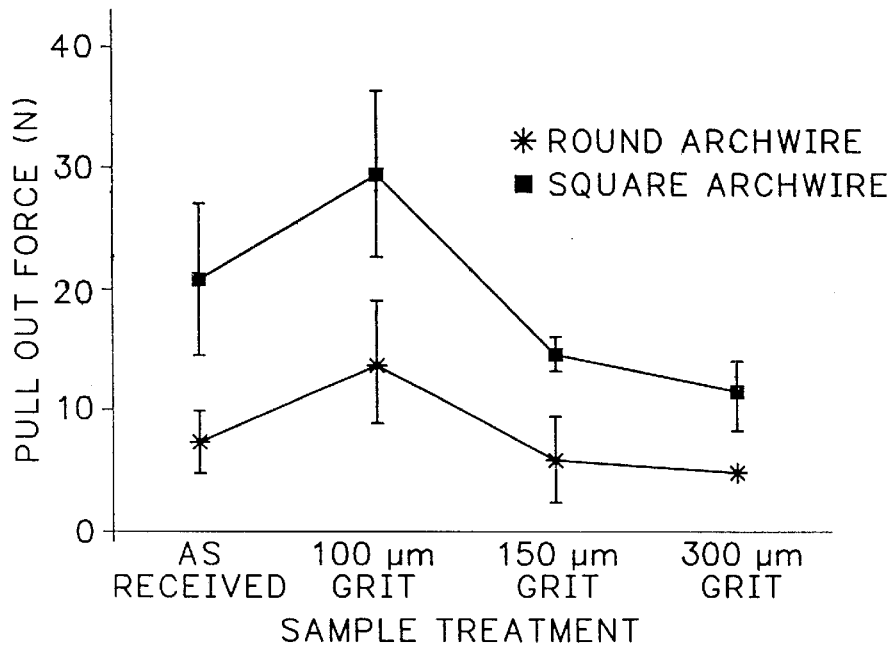
FIG. 5 is a graph showing the results of pull-out force measurements on shot peened NiTi alloy dental archwires.

The shot peening conditions and grades of media used were as noted above. As received dental archwires in both square and round section were uniformly peened and individually mounted into a stainless steel pull-out jig. A constant compressive closing force was maintained on each archwire in the jig whilst the force to pull the wires through the jig was measured. The results of these measurements as shown in FIG. 5
(i) Round section archwires Wire peened using the largest grit size of 300 $\mu$m showed a 40% reduction in pull-out force compared to that of unpeened wire. Wire peened with 150 $\mu$m grit showed a 21% reduction in pull-out force and wire peened with 100 $\mu$m grit showed an increase in pull-out force of 88%.
(ii) Square section archwires Wire peened using the largest grit size of 300 $\mu$m showed at 46% reduction in pull-out force compared to that of unpeened wire. Wire peened with 150 $\mu$m grit showed a 30% reduction in pull-out force and wire peened with 100 $\mu$m grit showed an increase in pull-out force of 42%.
Conclusion The magnitude of reduction in pull-out force of Ni-Ti archwire on stainless steel has been shown to be capable of modification by the use of shot peening, with a relationship existing between mass of peening particle and extent of surface treatment.

Example 4

CYTOTOXICITY EVALUATION OF SHOT PEENED NI-TI

The MTT (3-(4, 5-dimethylthiazol-2-yl)2, 5-diphenyl tetrazolium bromide)-based calorimetric assay is a useful method for the assessment of cytotoxicity and cell proliferation. The mitochondrial enzyme succinate-dehydrogenase within viable cells is able to cleave the tetrazolium salt MTT into blue coloured formazan which is soluble in iso-propanol and can be read in a spectrophotometer. The amount of formazan product is proportional to the number of viable cells present thus the higher the optical density, the greater the number of cells. Samples of shot peened and polished Ni-Ti of both austenitic and martensitic compositions were assessed by the MTT assay using 3T3 mouse fibroblast cells grown for 48 hrs on the test surfaces.

Figure 6:
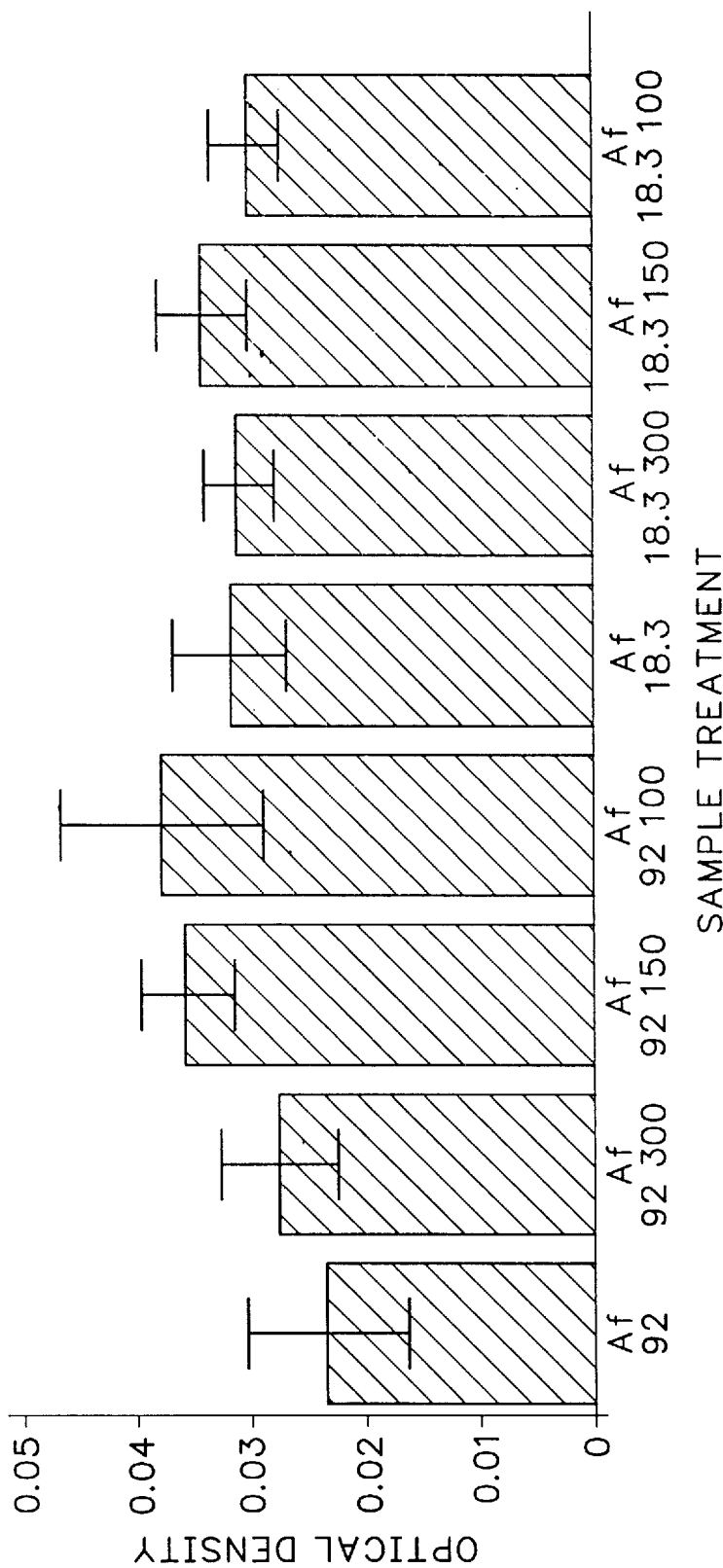
FIG. 6 shows the results of a cytotoxicity evaluation of shot peened NiTi alloy.

The mean optical density results are shown in FIG. 6. T-test statistical analysis at the 95% confidence level was used to determine whether there was any significant difference between the optical densities of the unpeened material and the peened material. The results of this analysis are shown in Table 2. With reference to this table, the mean optical density of each of the peened samples, for both austenitic and martensitic material, were observed to be statistically similar to those of the polished samples. It can be concluded from this that the shot peening of Ni-Ti does not have a detrimental effect upon the mitochondrial activity of 3T3 cells, that is the shot peened surfaces did not show any significant cytotoxicity in comparison the untreated surfaces.

TABLE 2

Statistical analysis summary of the 48 hr MTT optical density data. Student T-test comparison of the unpeened material against that of the peened material for both the austenitic and martensitic Ni—Ti samples, at the 95% confidence level.

| Treatment | Mean optical density | T-statistic | Probability |
|---|---|---|---|
| Af 18.3 | | | |
| As polished | 0.031 | | |
| 300 um grit | 0.030 | −0.127 | 0.90 |
| 150 um grit | 0.033 | 0.332 | 0.75 |
| 100 um grit | 0.029 | −0.394 | 0.71 |
| Af 92 | | | |
| As polished | 0.022 | | |
| 300 um grit | 0.022 | −0.027 | 0.98 |
| 150 um grit | 0.035 | 1.509 | 0.18 |
| 100 um grit | 0.037 | 1.276 | 0.25 |

Example 5

Figure 7:
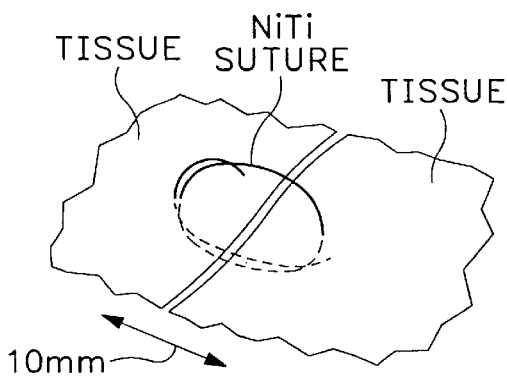
FIG. 7 is a schematic diagram of a tissue suture according to the invention.
Figure 8:
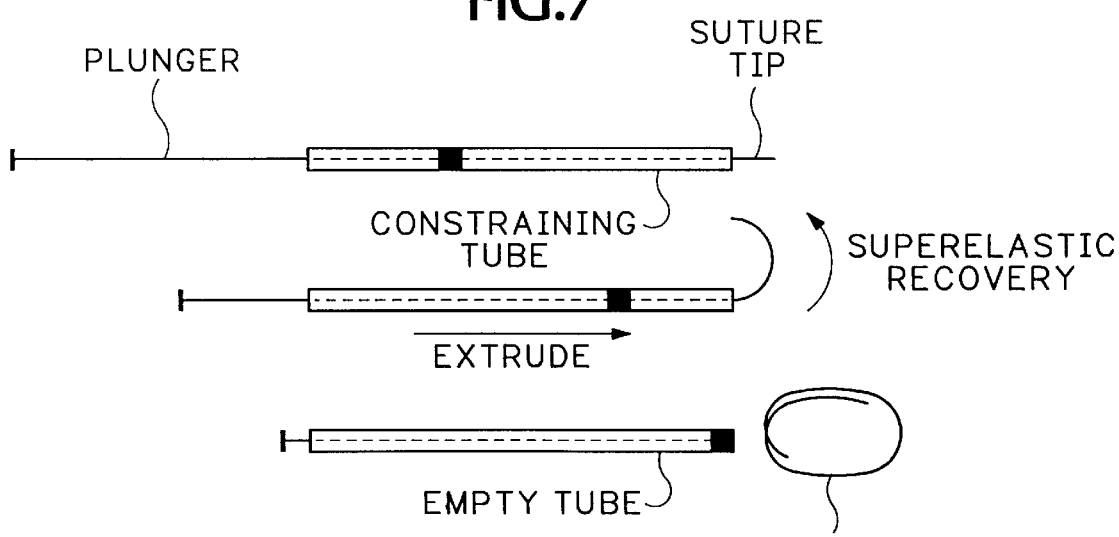
FIG. 8 is a diagrammatic illustration of extrusion of the suture.

A 30 mm length of 0.5 mm diameter superelastic NiTi wire of composition 50 atomic % Ni with an austenite finish temperature of below 0° C. was wound around a 10 mm diameter mandrel. The constrained wire was heat-treated in air at 450° C. for 15 minutes. After this time the mandrel and wire were removed from the furnace and allowed to cool to room temperature. The wire was uncoiled from the mandrel and fed into a 0.6 mm diameter rigid tube. One end of the heat-treated NiTi wire was protruded from the rigid tube, onto which a trocar style point was sharpened. Upon extrusion of the suture from the tube, the wire assumes the 10 mm diameter double coil of the mandrel upon which it was heat treated (FIG. 8). This particular suture will thus have penetration points of the wire coil through tissue 10 mm apart (FIG. 7).

There is thus described a method of surface hardening shape memory alloy, and in particular a biocompatible NiTi shape memory alloy, by causing a crystal to amorphous transition of a surface layer of the alloy. The bulk properties of the material such as the shape memory characteristics are not affected by the surface hardening, nor is its biocompatibility as measured by the cytotoxicity evaluation. The method also results in a significant reduction in the coefficient of friction of the alloy. This is a particular advantage in applications such as tissue suturing, orthodontics and textile binding. In the latter application the surface hardening gives improved wear characteristics to the material. The hardened alloy may also find use in other sewing, packaging, food and surgical applications. The method of the invention is moreover less expensive than other methods of surface treatment such as ion implantation.

Whilst endeavouring in the foregoing Specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. A method of surface treating a shape memory alloy comprising shot peening a sample of the alloy to be treated to cause a crystal to amorphous transition of a surface layer of the alloy without substantially affecting shape memory behavior of the sample.

2. A method as claimed in claim 1, in which the alloy comprises a NiTi shape memory alloy.

3. A method according to claim 1, further comprising preliminary forming and annealing of the sample to establish the shape memory.

4. A method according to claim 1, comprising polishing the alloy sample prior to peening.

5. A method according to claim 1, comprising shot peening the sample using glass peening media.

6. A method according to claim 4, comprising using a jet of fluid from a nozzle to carry the peening media and maintaining the sample at a constant distance from the nozzle.

7. A method according to claim 1, said shot peening step comprising using an air jet at a pressure of from 3 to 7 bar to carry peening media.

8. A method according to claim 1, comprising peening the sample for a time from 30 to 60 seconds.

9. A method according to claim 1, comprising ultrasonically cleaning the sample after peening.

10. A shape memory alloy which has been surface treated by a method according to claim 1.

11. A tissue suture which has been treated by a method according to claim 1.

12. Dental apparatus which has been treated by a method according to claim 1.

13. A dental archwire which has been treated by a method according to claim 1.

* * * * *